United States Patent [19]
Lewis et al.

[11] Patent Number: 6,013,711
[45] Date of Patent: Jan. 11, 2000

[54] HYDROPHILIC POLYSILOXANE COMPOSITIONS

[75] Inventors: Kenrick M. Lewis, New York; Hua Yu, White Plains, both of N.Y.

[73] Assignee: CK Witco Corporation

[21] Appl. No.: 09/093,941

[22] Filed: Jun. 9, 1998

Related U.S. Application Data

[60] Provisional application No. 60/050,106, Jun. 18, 1997.

[51] Int. Cl.$^7$ ................................................ G08L 83/06
[52] U.S. Cl. .......................... 524/265; 524/315; 524/493; 524/730; 524/731; 524/773; 524/789; 528/15
[58] Field of Search .............................. 528/15; 524/315, 524/265, 493, 773, 731, 730, 789

[56] References Cited

U.S. PATENT DOCUMENTS

| | | |
|---|---|---|
| 3,299,112 | 1/1967 | Bailey . |
| 4,259,467 | 3/1981 | Keogh et al. . |
| 4,260,725 | 4/1981 | Keogh et al. . |
| 4,657,959 | 4/1987 | Bryan et al. . |
| 4,752,633 | 6/1988 | Aasen et al. . |
| 4,847,398 | 7/1989 | Mehta et al. . |
| 4,857,583 | 8/1989 | Austin et al. . |
| 5,159,096 | 10/1992 | Austin et al. . |
| 5,191,103 | 3/1993 | Mehta et al. . |
| 5,367,001 | 11/1994 | Itoh et al. ................................ 523/109 |
| 5,565,194 | 10/1996 | Burkhardt et al. . |
| 5,580,921 | 12/1996 | Stepp et al. . |
| 5,830,951 | 11/1998 | Fiedler ................................ 525/478 |

OTHER PUBLICATIONS

General Picture of the Properties of the Silicones, 446–453, Ch. 9, *Chemistry and Technology of Silicones* (1968).

Chang, P. et al., Synthesis of Cyclo(dimethylSiloxane Co–methylhydrogensiloxane), Polymer Preprints, vol. 33, No. 2 (Aug. 5, 1992).

Aoki et al., Poly(divinylsiloxyethylene glycol)—synthesis and photoresist characteristics, J. Macromol. Rapid Commun. 18, 31–36 (1997).

*Primary Examiner*—Robert Dawson
*Assistant Examiner*—Jeffrey B. Robertson
*Attorney, Agent, or Firm*—Edward K. Welch, II; Andrew S. Reiskind

[57] ABSTRACT

The instant invention provides a method for improving the miscibility of the lower molecular weight unsaturated siloxane-polyether copolymers with the α,ω-divinylpolysiloxanes without loss of storage stability, or delay of cure at the vulcanization temperature, or loss of permanent hydrophilicity or other desirable features of the cured polysiloxane. The compositions of the present invention comprise one or more α,ω-divinylpolysiloxanes, unsaturated polysiloxane-polyether copolymers having from 2 to 5 silicon atoms per molecule which are preferably trisiloxanes, and a compatibilizing additive. The permanently hydrophilic, rapidly wettable polysiloxane compositions yield static water contact angles <50° dynamic advancing contact angles of less than about 100.

10 Claims, No Drawings

HYDROPHILIC POLYSILOXANE COMPOSITIONS

This application claims the benefit under 35 USC 119(e) of U.S. provisional application, Ser. No. 60/050,106, filed on Jun. 18, 1997.

FIELD OF THE INVENTION

This invention relates to polyorganosiloxane compositions that can be cured to rubbery, elastomeric or gelled materials whose surfaces are hydrophilic.

DESCRIPTION OF THE PRIOR ART

The terms "silicone rubber", "silicone gel" and "silicone elastomer" generally are used to describe elastic materials prepared by the crosslinking of linear polyorganosiloxanes. Gels, elastomers and rubbers are differentiated by the extent of crosslinking within the siloxane network, by hardness and elasticity. One quantitative measure of this difference is the modulus or resistance to deformation. Modulus is measured in units of force (e.g., newtons, N) per unit area (e.g., square meters, $m^2$). Rubbers typically have moduli in the range, $10^5$–$10^6$ Pa and gels have moduli in the range, $10^2$–$10^5$ Pa. The crosslinked, polysiloxane compositions of this invention are silicone gels and rubbery elastomers.

One deficiency of cured polyorganosiloxane gels and elastomers is their poor hydrophilicity. Several attempts have been made to introduce hydrophilicity into crosslinked polysiloxane compositions. For example, the incorporation of ethoxylated nonionic surfactants into the polysiloxane composition is disclosed in U.S. Pat. Nos. 4,657,959, and 4,782,101. U.S. Pat. Nos. 4,657,959; 4,691,039 and 4,752,633 disclose hydrolyzable and non-hydrolyzable siloxane-polyether copolymers of high ethylene oxide content as hydrophilizing agents for dental impression materials. The hydrophilicity is not permanent because the surfactants are not bonded to the polysiloxane matrix. Thus, as reported in German Patents, DE 4,306,997 and DE 4,320,920 and in *Journal of Prosthodontics*, 3(1994) 31–34, dental impressions made with these additives lose their wettability following disinfection and/or aqueous washing. The loss, measured as an increase of static or dynamic water contact angle, can be quite severe with hydrolyzable surfactants. U.S. Pat. No. 4,657,959 (Column 4, lines 4–8) acknowledges the diminution of hydrophilicity upon prolonged contact with aqueous media.

U.S. Pat. No. 5,122,392 discloses nonhydrolyzable polysiloxane-polyether copolymers in which the polysiloxane chains are terminated by hydroxyalkyl groups. These compositions react with carboxylic acids to confer durable hydrophilicity to polyester fibers and films. The bonds linking the functionalized polysiloxane-polyether to the polyester are ester (—C(O)—O) bonds. Polysiloxane-polyether copolymers bearing terminal methacrylate groups impart durable hydrophilicity to the contact lens compositions of U.S. Pat. Nos. 4,259,467 and 4,260,725. C—C bonds formed via free radical reactions link the functionalized polysiloxane-polyether to the remainder of the contact lens polymer. Ether (—C—O—C—) or ester (—C(O)—O) linkages attach these polysiloxane-polyether copolymers to the substrates. Aoki, et al., *Macromolecules, Rapid Communications*, 18 (1997) 31–36, synthesized hydrolyzable siloxane-polyether copolymers of general formula, [(R'$_2$SiO)—(C$_2$H$_4$O)$_7$]$_{20-35}$, wherein R'=vinyl. While all of these functionalized polysiloxane-polyether copolymers can be reacted into polymer matrices or onto surfaces to improve hydrophilicity, water absorption, lubricity and/or adhesion, the reactions do not result in the formation of Si—C bonds between the matrix or substrate and the functionalized polysiloxane-polyether.

U.S. Pat. No. 5,064,891 claims polysiloxane compositions with hydrophilicity is imparted by nonionic surface-active agents with siloxane and polyhydric alcohol blocks. No teaching is given about miscibility of these surface active agents with the majority components of the polysiloxane formulation, or about the storage stability of these formulations.

U.S. Pat. No. 5,580,921 discloses storage-stable polysiloxane compositions which impart permanent hydrophilicity to addition cure dental impression compounds. Permanent hydrophilicity is provided by hydrophilic modifiers (polysiloxane-polyether copolymers) which contain unsaturated functionalities and which are free of noble metal catalysts. Synthesis of the hydrophilic modifiers comprises the preparation of a distillable silane-polyether compound followed by its hydrolysis (alcoholysis), condensation and equilibration with alkenyl siloxanes. The hydrophilic modifiers have siloxane chain lengths greater than 10 and are miscible with the α, ω-divinylpolysiloxanes typically used in addition cure polysiloxane formulations. However, the present inventors have found that hydrophilic modifiers of lower siloxane chain length afford the most rapid spreading of water and wetting of the cured polysiloxane surface.

SUMMARY OF THE INVENTION

The instant invention provides a method for improving the miscibility of the lower molecular weight unsaturated siloxane-polyether copolymers with the α, ω-divinylpolysiloxanes without loss of storage stability, or delay of cure at the vulcanization temperature, or loss of permanent hydrophilicity or other desirable features of the cured polysiloxane. The compositions of the present invention comprise one or more α, ω-divinylpolysiloxanes, unsaturated polysiloxane-polyether copolymers having ≦5 silicon atoms per molecule which are preferably trisiloxanes, and a compatibilizing additive. Suitable compatibilizing additives include (a) substances with solubility parameters in the range of 13–17 MPa$^{1/2}$, such as isopropyl palmitate; (b) polysiloxane-polyether copolymers, preferably with no or low (<30 wt %) ethylene oxide and high (>80 wt %) content of propylene oxide, butylene oxide, or both, in the polyether segments; and (c) hydrophilic and/or hydrophobic fillers, preferably silicas, of surface area greater than 100 square meters per gram and median particle size smaller than about 20 nanometers. The permanently hydrophilic, rapidly wettable polysiloxane compositions yield static water contact angles <50°, preferably <40°, when measured in static mode, and by dynamic advancing contact angles of less than about 100 and preferably less than about 90°, when measured in dynamic mode.

DETAILED DESCRIPTION OF THE INVENTION

The present invention provides storage stable blends of α, ω-divinylpolysiloxanes and unsaturated polysiloxane-polyether copolymers, which blends can be used as one part of a two-part addition cure polysiloxane composition. The instant invention teaches the use of additives to compatibilize the hydrophilic unsaturated polysiloxane-polyether copolymers and the hydrophobic α, ω-divinylpolysiloxanes, or pendant vinylpolysiloxanes, to provide a storage-stable, hydrophilic vinyl polysiloxane. The present invention provides permanently hydrophilic polysiloxane compositions for use in dental, medical, personal care and textile applications. These compositions also have advantages such as extended working time and pot life, fast cure at the vulcanization temperature, no bubble-derived surface defects, desirable feel, taste, hardness, strength, elasticity and adhesion.

This invention relates to polysiloxane gel, elastomeric and rubber compositions which exhibit permanent water wettability. Such compositions are used in dental, medical, cosmetic and textile applications. Typically, the ingredients used to prepare the polysiloxane composition are combined selectively in a two part formulation so that, prior to combination to form the final cured product, the SiH-containing crosslinker is segregated from the hydrosilylation catalyst. Mixing of the two parts, designated Part A and Part B, occurs just prior to curing. However, a two part formulation is neither necessary nor critical to the realization of the hydrophilic properties disclosed in the instant invention.

Part A of the formulations of the instant invention is that which contains the SiH crosslinker and Part B is that which contains the hydrosilylation catalyst Part B of the formulations additionally contains the unsaturated polysiloxane-polyether copolymers which impart permanent hydrophilicity to the cured polysiloxane compositions. Compatibilizing additives are included in Part B to make it storage stable and prevent phase separation of its components. Since manufacture of the two part formulation and manufacture of the raw materials are typically done by different businesses at different locations, the compatibilizing and hydrophilizing agents advantageously are included in the polysiloxane raw materials to provide storage stable, hydrophilic blends.

Part A includes
1. a polyorganohydridosiloxane crosslinker that contains at least three SiH bonds per molecule,
2. optionally, a polyorganohydridosiloxane chain extender with terminal SiH groups,
3. a polydiorganosiloxane that contains at least two hydrosilylatable unsaturated hydrocarbon groups per molecule,
4. optionally, a rheology modifier such as vaseline, or a polydiorganosiloxane free of silanol groups or unsaturated groups capable of being hydrosilylated, or inhibiting the hydrosilylating reaction, and
5. optionally, temporary catalyst inhibitors, fillers, pigments, dyes, adhesion promoters and/or thixotropic additives.

Part B includes
1. a polydiorganosiloxane that contains at least two hydrosilylatable unsaturated hydrocarbon groups per molecule,
2. an effective amount of hydrosilylation catalyst,
3. a hydrophilic unsaturated siloxane-polyether copolymer as defined in copending U.S. patent application Ser. No. 09/082,563, filed May 21, 1998, in the names of Kenrick M. Lewis and Hua Yu, entitled "Siloxane-Polyether Copolymers With Unsaturated Functionalities, and Process for Making Them", which is hereby incorporated herein by reference,
4. a compatibilizing additive such as a hydrocarbon ester with solubility parameter, δ, =13–17 $MPa^{1/2}$, or a polysiloxane-polyether copolymer wherein the polyether portion contains a preponderance of hydrophobic units such as propylene oxide and butylene oxide, or a hydrophobic or hydrophilic filler, preferably silica, with surface area greater than 100 square meters per gram and median particle size smaller than 20 nanometers,
5. optionally, a rheology modifier such as vaseline, or a polydiorganosiloxane free of silanol groups or unsaturated groups capable of being hydrosilylated, or inhibiting the hydrosilylating reaction, and
6. optionally, temporary catalyst inhibitors, fillers, pigments, dyes, adhesion promoters and/or thixotropic additives.

The hydrosilylatable polydiorganosiloxane ((A) (3) and (B) (1)) has at least two unsaturated hydrocarbon groups per molecule. It may be represented by the formula

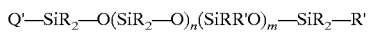

wherein Q is R or R', R is a $C_1$–$C_{20}$ saturated group (preferably $C_1$–$C_{12}$), R' is a $C_1$–$C_{20}$ unsaturated group (preferably $C_1$–$C_{12}$) that can undergo a hydrosilylation reaction. For example, R can be methyl, ethyl, phenyl, tolyl, trifluoropropyl or heptafluoropropyl, and R' can be vinyl, allyl, vinylcyclohexyl, styryl or propargyl. The subscript, n, is a positive number typically greater than about 100, and preferably between about 200 and about 2,000. If all Q are R then M>2 but if both Q are R, M is 0 to 10. This siloxane may be linear, branched or a star structure.

Preferably, the hydrosilylatable polydiorganosiloxane is a linear polydimethylsiloxane that has a vinyl group attached to the silicon atom at each chain terminus. Additionally, the hydrosilylatable polydiorganosiloxane can be a copolymer, a block copolymer or mixed-substituent copolymer wherein the organo groups, R, as defined herein above, are not all the same.

Some examples of hydrosilylatable polydiorganosiloxane include the following:

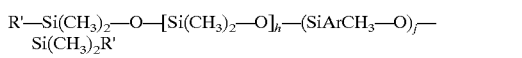

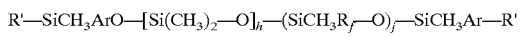

in which R' has the same meaning as defined hereinabove, Ar is an aryl group such as phenyl, and $R_f$ is a fluoroalkyl group such as, for example, trifluoropropyl. The subscripts h and j can be positive numbers. Their sum is typically greater than 100, and preferably between about 200 and 2000.

The hydrosilylatable polydiorganosiloxane can have a unimodal molecular weight distribution. These materials are well-known in the art and are available commercially. Representative syntheses are reported in, for example, *Polymer Preprints*, No. 10 (1969), 1361 and *Acta Polymerica*. 42(1991) 107–109, the complete disclosures of which are incorporated herein by reference. Alternatively, the hydrosilylatable polydiorganosiloxane can be a blend of products such that the blend has a bimodal or higher modal molecular weight distribution. The viscosity of the polydiorganosiloxane, either as a single product or as a blend, can be between about 150 and about 500,000 centistokes and, preferably, between about 500 and about 100,000 centistokes. It is desirable that the polydiorganosiloxane be substantially free from silanol groups, SiOH. The silanol content should be less than 150 ppm and, preferably, less than 50 ppm.

The crosslinker (A) (1) can be a linear or branched polyorganohydridosiloxane that contains at least three Si—H bonds per molecule. The number of Si—H bonds per molecule is the functionality of the crosslinker. In particular, the crosslinker may be represented by the formulae

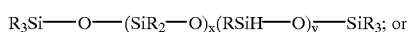

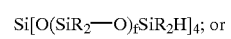

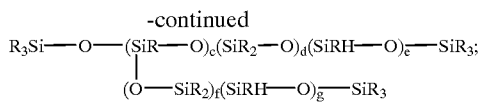

or cyclic structures, $(RSiHO)_y$ and $(R_2SiO)_x(RSiHO)_y$, such as $(CH_3SiHO)_4$ and $[(CH_3)_2SiO]_3(CH_3SiHO)_3$, or a polyhedral structure containing $(HSiO_{1.5})$ subunits as disclosed in U.S. Pat. No. 5,106,604 and in *Journal of Materials Chemistry*, 3(1993) 1319. R is a $C_1$–$C_{20}$ saturated group (preferably $C_1$–$C_{12}$), x is $\geq 0$ (preferably between about 1 and 100), y is at least 3, the sum of e and g is at least 3, and c, d, e, f, g are any positive numbers. Preferably, f is between about 0 about 100. The Si—H bonds can be distributed in various ways along the polymer chain, including random distribution among internal and terminal positions. In part A, A(1) should be present at 0.05 to 0.5 gm/gm of the unsaturated siloxane A(3).

Polyorganohydridosiloxanes (A) (2) with terminal SiH groups function as chain extenders. The person of ordinary skill in the art readily can determine the need for and the quantity of chain extender in a formulation. Examples of polyorganohydridosiloxanes, including some with terminal Si—H bonds, are the following:

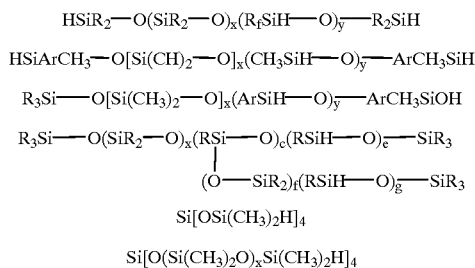

in which R, $R_f$, and Ar have the same meanings as defined hereinabove. Subscripts x and f can be between about 1 and about 100 and are, preferably, between about 15 and about 75. Subscript c is a positive number. In branched polyorganohydridosiloxanes, the sum of x and f is preferably between about 15 and about 75. The subscripts, e, y and g can be any positive numbers provided that the total of Si—H bonds per molecule is at least three.

Although use of a single polyorganohydridosiloxane of unimodal molecular weight distribution and well-defined functionality for crosslinking is customary, blends of polyorganohydridosiloxanes of high and low functionalities and molecular weights can sometimes offer cured polysiloxane compositions with balanced strength, softness, elasticity and adhesion, as is readily determined by the person having ordinary skill in the art Products satisfying the functionality and molecular weight requirements of the crosslinkers are well-known in the art and are available commercially. Syntheses of these products have been published in, for example, W. Noll, *Chemistry and Technology of Silicones*, Academic Press, NY, 1968, which is incorporated herein by reference.

The hydrosilylation catalyst (B) (2) can be a platinum group metal or a compound of such a metal. Further, it must be an addition cure hydrosilylation catalyst. Examples include platinum (II) and zerovalent platinum complexes, as well as colloidal platinum disclosed in U.S. Pat. Nos. 4,273,902 and 4,288,345. The organometallic complexes of platinum with 1,3-divinyltetramethyldisiloxane and low molecular weight vinyl end-blocked organosiloxanes are preferred. These complexes are described in, for example, U.S. Pat. Nos. 3,419,593; 3,516,946; 3,775,452; 30814,730; 4,782,101 and in *Angewandte Chemie, International Ed.*, 30(1991) 438–440. Complexes with alkynes are described in, for example, U.S. Pat. No. 4,631,310. B. Marciniec, *Comprehensive Handbook on Hydrosilylation*, Pergamon Press, NY 1992 provides a comprehensive list of addition cure catalysts. Each of these references is incorporated herein by reference.

Various temporary catalyst inhibitors optionally can be included in PART A and/or PART B to increase the storage stability and working time of the polysiloxane composition prior to curing. Acetylenic alcohols such as 2-methyl-3-butyn-2-ol are described for such purpose in U.S. Pat. No. 3,445,420, cyclic methylvinylsiloxanes in U.S. Pat. No. 3,989,667, allynyl silanes in U.S. Pat. No. 4,472,562, conjugated enynes in U.S. Pat. No. 4,472,563, and maleate esters in U.S. Pat. No. 4,256,870. A listing of additional its temporary inhibitors is published in B Marciniec, loc. cit., p. 190. Each of these references is incorporated herein by reference. Compounds with $SiH_3$ (primary silane) groups are disclosed as temporary catalyst inhibitors in U.S. Pat. Nos. 5,223,344 and 5,534,609. These can be added to PART A, but should not be included in PART B. Both cited patents are incorporated herein by reference.

Mixtures of work time extenders can be employed advantageously for improved performance and processing of the curable polysiloxane composition, as known to the person having ordinary skill in the art. For example, methylvinylcyclosiloxanes, dialkylmaleates or alkynols can be used in PART B with the $SiH_3$-containing compounds in PART A. One of ordinary skill would be aware how best to optimize mixtures to obtain particularly desired results. For instance, it may be desirable to combine diethylmaleate with the primary silane to obtain extended pot-life, enhanced adhesion to substrate and shortened cure time at temperatures >80° C. Longer cure times, extended pot-life and enhanced adhesion can be obtained with combinations of primary silanes and methylvinylcyclosiloxanes. These conditions may be desirable if the formulation must flow into and fill cavities at moderate temperatures prior to crosslinking.

Polydiorganosiloxanes free of silanol groups or free of unsaturated groups capable of being hydrosilylated or inhibiting the hydrosilylating reaction function as rheology modifiers. This means that they influence the processing, flow (viscosity), extension (elasticity), tension, dampening and deformation properties of the cured elastomer or gel. The magnitude of this influence depends both on the molecular weight of the polydiorganosiloxane and on its concentration in the polysiloxane composition. Preferably, the polydiorganosiloxane is fluid, miscible with and unreactive with the other components of the formulation. In dental formulations, vaseline and other petroleum-based products are often used as rheology modifiers in place of the polydiorganosiloxanes.

The crosslinking reactions between the SiH bonds in PART A and the unsaturated linkages in PART B are accompanied by enormous changes in the rheology of the polysiloxane composition. Most notably, increases occur in viscosity, elasticity and modulus. The magnitude of the increases is determined by, among other variables (for example, fillers), the crosslink density and the concentration of crosslinked polymer. Higher crosslink densities usually are associated with high modulus, high viscosity and low elasticity. Conversely, low crosslink density typically leads to the opposite of these properties. Elasticity is increased by a higher molecular weight between crosslinks. When the crosslinking reaction is conducted in the presence of inert, plasticizing components such as the polydiorganosiloxanes or vaseline, the concentration of crosslinked, viscoelastic polymer in the siloxane composition is effectively reduced. Control of polymer concentration affords process control over the rheological properties of the elastomeric or gel product For example, increases in polymer concentration bring about increases of viscosity, dampening and modulus. Increasing the molecular weight or viscosity of the polydiorganosiloxane rheology modifier will also increase the probability of entanglements between its molecular chains and those of the crosslinked, viscoelastic polymer. This increased entanglement raises the overall viscosity of siloxane composition, improves its dampening ability and its capacity to return to its original condition following deformation. Specific information on the interrelationships among Theological parameters and SiH/vinyl stoichiometry in dental formulations is available in J. R. Williams and R. G. Craig, *Journal of Oral Rehabilitation*, 15 (1988) 639–650, and in W. J. Finger, et al., *Dental Materials*, 2(1986) 179–186, which are incorporated herein by reference.

Polydiorganosiloxane rheology modifiers ((A) (4) or (B) (6)) can be linear or branched. In particular, they can be represented by the formula

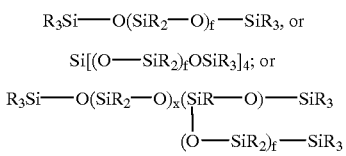

wherein R is a $C_1$–$C_{20}$ saturated group (preferably, $C_1$–$C_{12}$), f is between about 50 and about 2500 (preferably between about 100 and about 1500), and d and x have the same meanings as defined hereinabove.

Optionally, reinforcing and non-reinforcing inorganic fillers and thixotropic additives, can also be included in the composition. Reinforcing and non-reinforcing inorganic fillers are solids such as famed silica, precipitated silica, finely powdered quartz, calcium carbonate, talc, alumina, silicon nitride, aluminum nitride and titanium dioxide. Hydrophobized fumed silica is preferred because it prevents crepe hardening in the stored polyorganosiloxane composition prior to its curing. Blends of hydrophobized and hydrophilic silica also provide a safeguard against excessive solids settling in the stored material prior to curing. Some elastomers, especially elastomers that must be electrically conductive, are filled with finely powdered metal such as copper, silver, gold, or platinum particles. Such products are described in U.S. Pat. Nos. 4,770,641; 5,037,312; and 5,074,799, which are incorporated herein by reference. Specific thixotropes that can be employed in conjunction with fumed silica and other fillers include the commercial products sold under the trade names, KEVLAR ULTRATHIXT™, TROYTHIX™ XYZ and THIXCIN™. KEVLAR ULTRATHIX™ filler is a fibrous form of poly(p-phenyleneterephthalamide) manufactured and sold by DuPont as a thixotrope. TROYTHIX™ and THIXCIN™ fillers are both triglycerides derived from glycerol and castor oil fatty acids. TROYTHIX is a trademark of Troy Corporation and THIXCIN is a trademark of Baker Castor Oil Co. Pigments and dyes can be added to color the gels and elastomers and to distinguish Parts A and B from each other.

Fillers suitable for compounding dental impression materials, for example, the hydrophobized silicas of surface area greater than 50 square meters per gram available commercially as AEROSIL® (from Degussa) and CABO-SIL® (from Cabot Corp.), are already disclosed and well-known. These fillers can account for 15–80 weight percent of dental formulations. Directions for their effective use are published in the manufacturer's product literature. Illustrative dental formulations or data showing the effect of fillers on the physical properties of silicone impression materials have been reported, for example, in U.S. Pat. No. 4,782,101, U.S. Pat. No. 4,752,633, in R. G. Craig, Restorative Dental Materials, C. V. Moose-Comp., St. Louis, 1980, pp 195ff., and in W. J. Finger, *Dental Materials*, 4(1988) 33–37.

The hydrophilic additives (B) (3) of the instant invention are linear, cyclic and branched unsaturated siloxane-polyether copolymers having 2 to 5 silicon atoms per molecule. Each copolymer has at least one polyether group and at least one aliphatic unsaturated group. These copolymers satisfy the general formulae:

LINEAR
(A) $R^1$—$SiR_2O(SiR_2$—$O)_p$—$(SiR^2Z$—$O)_m$—$SiR_2R^1$
(B) $R^1$—$SiR_2O(SiR_2$—$O)_p$—$(SiR^2Z$—$O)_m$—$SiR_3$
(C) $R_3SiO(SiR_2$—$O)_p$—$(SiR^2Z$—$O)_m$—$(SiR^2R^1$—$O)_q$—$SiR_3$
(D) $R_1$—$R_2SiO(SiR_2$—$O)_p$—$(SiR^2Z$—$O)_m$—$(SiR^2R^1$—$O)_q$—$SiR_3$
(E) $R^1$—$R_2SiO(SiR_2$—$O)_p$—$(SiR^2Z$—$O)_m$—$(SiR^2R^1$—$O)_q$—$SiR_2R^1$
(F) $Z$—$SiR_2O(SiR_2$—$O)_p$—$(SiR^2R^1$—$O)_q$—$SiR_2R^1$
(G) $[Z$—$SiR^2O(SiR_2$—$O)_p]_r$—$(SiR_2$—$O)$—$(SiR^2R^1$—$O)_q$—$SiR_2R^1$

CYCLIC
(H)$(R_2Si$—$O)_p$—$(SiR^2Z$—$O)_m$—$(SiR^2R^1$—$O)_q$

BRANCHED
(I) $R^1Si[(O$—$SiR_2)_p$—$Z]_3$
(J) $RSi[(O$—$SiR^2R^1)_q$—$(O$—$SiR_2)_p$—$Z]_3$
(K) $[R^1SiR_2O(SiR_2$—$O)_p]_v$—$(SiO_2)[(O$—$SiR^2R^1)_q(O$—$SiR_2Z)_m]_{4-v}$ wherein R is a $C_1$–$C_{20}$, preferably $C_1$–$C_{12}$, saturated, monovalent organic group. Illustrative of the saturated monovalent groups represented by R are the alkyl groups (for example, methyl, ethyl, isopropyl, octyl and dodecyl groups), the aryl groups (for example, the phenyl and naphthyl groups), the alkaryl groups (for example, the tolyl and nonylphenyl groups), the araalkyl groups (for example, the benzyl and phenethyl groups) and the cycloalkyl groups (for example, the cyclopentyl and cyclohexyl groups). R may also be a functionalized organic group such as the chloropropyl, heptafluoroisopropyl, and cyanoethyl groups.

$R_1$ is a $C_1$–$C_{20}$, preferably $C_1$–$C_{12}$, unsaturated monovalent organic group that can be hydrosilylated to yield silicon-carbon bonds. Illustrative of the unsaturated groups represented by $R^1$ are the alkenyl groups (for example, the vinyl, allyl, methallyl, vinylcyclohexanyl, and, the alkynyl groups (for example, the acetylenic and the propargyl).

The groups $R^2$ may be the same as R or as $R^1$. Thus, for example, they provide for the presence of methyl and vinyl groups on the same silicon atom, or for the existence of geminal divinyl substitution.

Values of m, p, q, r and v are chosen such that the total number of silicon atoms per molecule is 2 to 5 inclusive with the proviso that there is at least one Z and at least one $R^1$ per molecule. R and v ave values from 0 to 1, $3 \geq m > 0$, and $0 \leq q$ and $p \leq 3$. More preferably, this a vinyl endblocked siloxane, with p=0 and R is methyl, most preferably a trisiloxane.

Z is a polyether-containing group that is linked to the polysiloxane block by a silicon-carbon bond. Z has general formula of the type,

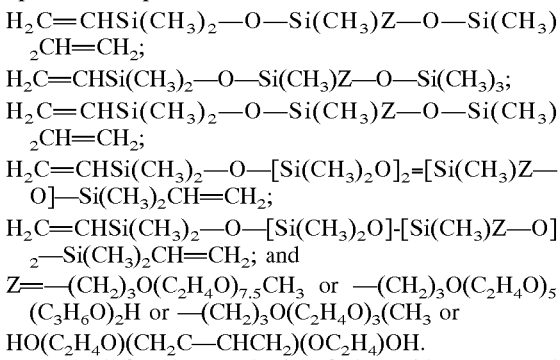
—$C_xH_{2x}O(C_aH_{2a}O)_bR''$ and —$C_xH_{2x}OG[(C_aH_{2a}O)_bR'']_z$ wherein x is an integer in the range 1–20, and is preferably 2–8. The subscript, a, is an integer having a value greater than or equal to 2. Preferred values of a are 2, 3, and 4. Illustrative of the oxyalkylene groups in the polyether portion of the copolymer are the oxyethylene, the oxy-1,2-propylene, oxy-1,2-butylene, oxy-2,2-dimethyl-1,3-propylene groups and the like. The polyether portion of the copolymer may contain oxyalkylene units of more than one type. For optimum hydrophilicity, it is desirable that at least 40 weight percent, and preferably at least 50 weight percent, of the oxyalkylene groups be oxyethylene groups. The subscript, b, is a positive number that is preferably in the range, 3–12.

G is a polyhydroxy group capable of being alkoxylated. The subscript, z, represents the number of alkoxylated hydroxyl groups. Examples of G are alkylene glycols, alkyne glycols, glycerol, pentaerythritol, hydroquinone, trimethylolpropane, sorbitol, glucose and sucrose.

R' is hydrogen or a polyether capping group such as an alkyl group of 1–8 carbon atoms, or an acyl group of 1–8 carbon atoms, or a vinyl ether or an organosilyl group. Alkyl groups exemplifying R' are methyl, tertiary butyl and 2-ethylhexyl. Examples of acyl capping groups are acetoxy, acetoacetoxy, acryloxy, methacryloxy and benzoyl. Organosilyl capping groups comprise the saturated trialkylsilyl groups such as trimethylsilyl, triethyl, ethylisopropyl, thexyldimethyl, t-butyldimethyl, t-butyldiphenyl, the unsaturated capping groups such as the vinyldimethyl, divinyloctyl, ethynyldimethyl and propynyldimethyl. Examples of vinyl ether end groups comprise dihydropyranyl and vinyloxyethoxy ($H_2C=CH—O—CH_2CH_2O—$). Owing to the variable efficiency of polyether capping reactions, uncapped polyether molecules are likely to be present during the hydrosilylation synthesis of the polysiloxane-polyether copolymer starting material. Accordingly, nominally capped copolymer products may also contain uncapped polysiloxane-polyether copolymers.

Specific examples of the inventive structures are $H_2C=CHSi(CH_3)_2$—O—$Si(CH_3)Z$—O—$Si(CH_3)_2CH=CH_2$;

$H_2C=CHSi(CH_3)_2$—O—$Si(CH_3)Z$—O—$Si(CH_3)_3$;

$H_2C=CHSi(CH_3)_2$—O—$Si(CH_3)Z$—O—$Si(CH_3)_2CH=CH_2$;

$H_2C=CHSi(CH_3)_2$—O—$[Si(CH_3)_2O]_2$=$[Si(CH_3)Z$—O]—$Si(CH_3)_2CH=CH_2$;

$H_2C=CHSi(CH_3)_2$—O—$[Si(CH_3)_2O]$-$[Si(CH_3)Z$—O]$_2$—$Si(CH_3)_2CH=CH_2$; and Z=—$(CH_2)_3O(C_2H_4O)_{7.5}CH_3$ or —$(CH_2)_3O(C_2H_4O)_5(C_3H_6O)_2H$ or —$(CH_2)_3O(C_2H_4O)_3(CH_3$ or $HO(C_2H_4O)(CH_2C—CHCH_2)(OC_2H_4)OH$.

A method for the synthesis of the said unsaturated polysiloxane-polyether copolymers of controlled unsaturation content includes the following steps: (a) combining polysiloxane-polyether copolymers and an alkenyl or allynyl silane or siloxane, capable of undergoing addition or redistribution reactions with the copolymers in an amount sufficient to achieve the desirable degree of alkenyl or alkynyl substitution to form a first mixture, (b) adding to the first mixture of reagents a catalytically effective amount of a basic catalyst to form a reaction mixture; and (c) heating the reaction mixture.

These polysiloxane-polyether copolymer is synthesized, for example by hydrosilylation as described in U.S. Pat. Nos. 3,299,112, 4,847,398, 4,857,583, 5,191,103 or 5,159,096, all of which are hereby incorporated by reference. The hydrosilylation product can contain the copolymer, bound and free platinum, unreacted polyether and reaction byproducts such as acetals and propanal. In the second step, this hydrosilylation product is reacted with linear and/or cyclic siloxanes and silanes bearing unsaturated groups bonded to silicon (for example, $[H_2C=CHSi(CH_3)_2]_2O$ or $[H_2C=CHSi(CH_3)O]_{3-25}$, or $(H_2C=CH)_xSi[OSi(CH_3)_3]_{4-x}$, $(H_2C=CH)_xSi(OC_2H_4OCH_3)_{4-x}$, x=1, 2, or 3 so that either a redistribution of saturated and unsaturated groups occurs, or siloxane segments bearing unsaturated groups become incorporated into the polysiloxane blocks of the polysiloxane-polyether copolymers.

Redistribution or ring opening is accomplished in the presence of basic catalysts such as KOH, CsOH, $Ca(OH)_2$, $(CH_3)_4N^{+-}OSi(CH_3)_3$, $(CH_3)_4N^{+-}[OSi(CH_3)_2]_s^{-+}N(CH_3)_4$ (s=4–100) and $K^{+-}OSi(CH_3)_3$ at temperatures up to about 200° C., preferably up to about 150° C. Catalysts containing the tetramethyl ammonium cation, or another tetra alkyl ammonium cation, are preferred because they are readily destroyed by heat at the end of the reaction. The reaction mixture is stripped in vacuo to remove unreacted alkenyl siloxane and volatile byproducts. A complete disclosure of the synthesis of the instant hydrophilic additives is given in copending U.S. patent application Ser. No. 09/082563, filed May 21, 1998, in the names of Kenrick M. Lewis and Hua Yu, entitled "Siloxane-Polyether Copolymers With Unsaturated Functionalities, and Process for Making Them", which is hereby incorporated herein by reference.

The presence of bound and free platinum in the hydrophilic, unsaturated polysiloxane-polyether copolymer products mitigates against inclusion of this additive in PART A of the formulation, if long storage stability is desired. Laboratory tests performed with the hydrophilic additives in PART A showed storage and performance stability for at least one month. However, even when present at very low part per million levels, platinum has the potential to catalyze premature addition of SiH and hydrosilylatable unsaturated groups, or catalyze other reactions leading to hydrogen formation in PART A. Accordingly, the hydrophilic, unsaturated polysiloxane-polyether copolymer products of the instant invention are included in PART B to assure maximum storage and performance stability.

Since they contain fewer than 5 silicon atoms, the hydrophilic, unsaturated polysiloxane-polyether copolymers of this invention generally are not miscible with the hydrosilylatable polydiorganosiloxanes comprising the addition cure formulation. Miscibility and homogeneity in PART B, and/or in blends of hydrophilic, unsaturated polysiloxane-polyether copolymer with hydrosilylatable polydiorganosiloxanes, are desirable if the formulation and raw materials are to be storage stable and consistently good in their performance and processing over time. These are achieved by the use of one or more compatibilizing agents (B) (4) selected from the following groups.
1. a compatibilizing additive such as a hydrocarbon ester with solubility parameter, $\delta_i$=13–17 $MPa^{1/2}$,
2. or a polysiloxane-polyether copolymer wherein the polyether portion contains a preponderance of hydrophobic units such as propylene oxide and butylene oxide,
3. or hydrophobic or hydrophilic fillers, preferably silicas, of surface area greater than 100 square meters per gram and median particle size less than 20 nanometers.

It is an objective of the instant invention that the compatibilizing agents be used in sufficient quantity to effect homogeneity of the hydrophilic, unsaturated polysiloxane-polyether copolymers and the hydrosilylatable polydiorganosiloxane in PART B. The compatibilizing agents must not have a deleterious effect on processing or properties of the cured polysiloxane composition. Properties of interest to compositions used in dental, medical, cosmetic, personal care and textile applications include storage stability, working time, pot life, cure time, hydrophilicity, hardness (softness), dimensional change with temperature, tear strength, tensile strength, elasticity, adhesion, surface appearance, feel and consistently good performance over time. All of these terms are familiar to those of average skill in the art of formulating and applying addition cure polysiloxane compositions.

Solubility parameters, δ, indicate the cohesive energy densities of materials and afford predictions about the miscibility of different materials. A material with a high δ value requires more energy for dispersal than is gained by mixing it with a material of lower δ value, so immiscibility or phase separation results. Two materials of similar δ value gain sufficient energy on mutual dispersion to permit homogeneous mixing. In SI units, δ is expressed as the square root of megapascals ($MPa^{1/2}$). Values of solubility parameters for a wide variety of materials are tabulated in A. F. M. Barton, *Handbook of Solubility Parameters and Other Cohesion Parameters*, CRC Press, Boca Raton, Fla., 1991.

The hydrocarbon esters suitable for use as compatibilizers have solubility parameters in the range, $δ=13–17$ $MPa^{1/2}$, and general formulae, $R^3(COOR^4)_k$, or $R^3COO(C_aH_{2a}O)_bOCR^3$ wherein $R^3$ is a mono, di, tri or polyvalent hydrocarbon radical derived from a carboxylic acid. $R^3$ can be a straight or branched alkyl, aryl, alkaryl or cycloaliphatic group of valency equal to the number, k, of ester functional groups. Examples of $R^3$ include $C_{12}H_{25}$, $C_{14}H_{29}$, $C_{15}H_{31}$, $C_{16}H_{33}$, adipyl, azelayl, cyclohexanediyl radicals derived from natural and synthetic fatty acids. $R^4$ is a monovalent hydrocarbon radical derived from an alcohol. Examples of $R^4$ are methyl, isopropyl, neopentyl, octyl, cyclohexyl, lauryl and stearyl. The numbers a and b have the same meanings as have been defined hereinabove for oxyalkylenes. Only those satisfying $δ=13–17$ $MPa^{1/2}$ give storage and performance stable blends of hydrophilic, unsaturated polysiloxane-polyether copolymers with the hydrosilylatable polydiorganosiloxanes, and/or storage and performance stable PART B compositions. Examples of preferred esters are isopropyl palmitate, isopropyl myristate and dibutyl sebacate.

Mixtures of the hydrocarbon esters, hydrosilylatable polydiorganosiloxanes and hydrophilic, unsaturated polysiloxane-polyethercopolymers (PART B) can be made in a number of different ways. For example, the hydrosilylatable polydiorganosiloxanes can comprise the majority (about 50–75 weight percent) of the blend, the hydrocarbon ester can comprise about 5–30 weight percent and the hydrophilic, unsaturated polysiloxane-polyether copolymers about 1–20 weight percent. Alternatively, the hydrocarbon ester can be the major component (about 50–75 weight percent) of the blend depending on the specific application.

Polysiloxane-polyether copolymers wherein the polyether portion of the molecule contains greater than 80 weight percent, preferably 100 weight percent hydrophobic oxyalkylene units such as propylene oxide and butylene oxide, are effective compatibilizers in the context of the instant invention. These well-known copolymers, whose synthesis is disclosed for example in U.S. Pat. Nos. 3,209,112, 3,507, 815, 4,847,398 and 5,191,1 03, do not usually contain hydrosilylatable unsaturated groups. Such groups can be present, but are not required, for the compatibilization function disclosed in the instant invention. When they are present, care must be taken to ensure that concentration of unsaturated groups does not inhibit the noble-metal catalyzed addition cure reaction to a greater extent than is required or desired for the application of interest.

Compatibilizing copolymers can have general structures such as, $MD_xD^*_yM$, $M^*D_xD^*_yM$, $M^*D_xD^*_yM^*$ and $M^*D_xM^*$, wherein $M=R_3SiO_{1/2}$, $D=R_2SiO$, $D^*=RSiOZ'$, $M^*=R_2Z'SiO_{1/2}$ and R and Z have the same meanings as hereinabove defined for the siloxane structures. x is 1 to 100 and y is 1 to 20. The polyethers, Z', of the compatibilizing agents preferably have no or low (<30 wt %) ethylene oxide and high (>80 wt %) propylene oxide or butylene oxide content. This is desirable for maximum long term miscibility of hydrosilylatable polydiorganosiloxanes and hydrophilic additives containing fewer than 10 silicon atoms per molecule. However, there are examples in which miscibility was achieved with compatibilizing copolymers having only ethylene oxide segments in the polyether. It should also be mentioned that the compatibilizing copolymers are not required to impart permanent or semipermanent hydrophilicity. Moreover, it will be illustrated by experiment that cured polysiloxane compositions containing the inventive hydrophilic additives and compatibilizing agents exhibit permanent hydrophilicity, whereas it is known from U.S. Pat. No. 4,657,959 that the polysiloxane-polyether copolymers of high ethylene oxide content impart only semipermanent hydrophilicity.

Illustrative of the structures of the preferred compatibilizing agents of the instant invention are the following:

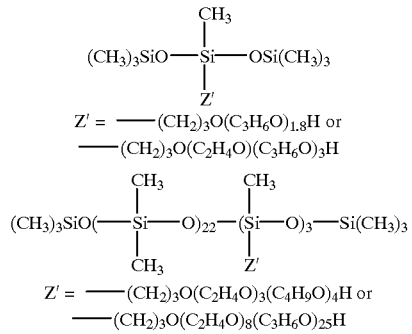

The selection of compatibilizing copolymer and its concentration which effectively affords storage stable miscibility depend principally on the structures and quantities of the hydrosilylatable polydiorganosiloxane and the hydrophilic, unsaturated polysiloxane-polyether copolymer to be mixed. For example, trisiloxane compatibilizers appear to be optimum for the hydrophilic, unsaturated trisiloxane copolymers. Higher oligomeric compatibilizers may be more effective for hydrophilic additives containing up to nine silicon atoms. It is preferable to keep the usage of the compatibilizing copolymer below 30 weight percent of the mixture, and most preferably at 0.1–10 weight percent. However, as with the hydrocarbon ester compatibilizers, situations can arise in which it will be advantageous to use mixtures wherein the compatibilizing copolymer comprises the majority of the blend of hydrosilylatable polydiorganosiloxanes and hydrophilic, unsaturated polysiloxane-polyether copolymers.

Hydrophobic or hydrophilic fillers, preferably silicas, of surface area greater than 100 square meters per gram and median particle size less than 20 nanometers are also effective compatibilizing agents in the context of this invention. High surface area and small particle size facilitate use of minimal weights of these compatibilizers and the incorporation of maximal quantities of the hydrophilic, unsaturated copolymers. Minimal usage is also important if the viscosity of the mixtures must be kept manageable and appropriate for mixing of the two part formulation. Thus, in contrast to the 15–80 weight percent quartz flour, calcium carbonate and/or other hydrophobic reinforcing filler typically used in dental and high durometer silicone formulations, the compatibilizing fillers of this invention are preferably hydrophilic silicas used at 0.5–10 weight percent in the mixtures of hydrophilic, unsaturated copolymer and hydrosilylatable polydiorganosiloxane. Hydrophilic silicas such as AEROSIL®200, AEROSIL®300, Silica FK 160 and Silica FK 320 DS produced by Degussa are preferred compatibilizing fillers.

Of course, applications can arise in which compatibilizing filler concentrations higher than those designated above as preferable can be beneficial. These instances also fall within the scope of this invention if the composition comprises fillers of surface area greater than 100 square meters per gram and median particle size less than 20 nanometers, hydrophilic, unsaturated polysiloxane-polyether copolymers and hydrosilylatable polydiorganosiloxane. There may also be advantage to compounding the compatibilizing filler and hydrophilic, unsaturated polysiloxane-polyether copolymers separately as a grease or dough, or coating the surfaces of the compatibilizing and reinforcing fillers with the hydrophilic, unsaturated polysiloxane-polyether copolymers for subsequent dispersal of the grease, dough or coated solids in the hydrosilylatable polydiorganosiloxanes and manufacture of a PART B composition. Combinations of the various compatibilizing agents can also be advantageous in some applications. All of these alternatives fall within the purview of the instant invention.

Hydrophilicity typically is determined by measuring the contact angle of a water drop on the surface of interest (see W. Noll, *Chemistry and Technology of Silicones*, Academic Press, NY, 1968, pp 447–452). A value less than about 60° after 2–3 minutes wetting time denotes a hydrophilic surface. It is well known (W. Noll, loc. cit.) in the art that unmodified polysiloxane surfaces are very hydrophobic and yield equilibrium static water contact angles greater than about 80°. Commercially available hydrophilic dental impression materials yield equilibrium values in the range of 40–60° when cured. However, these hydrophilic values increase to the hydrophobic range following washing and/or disinfection of the dental impression. The unsaturated polysiloxane-polyether copolymers of the instant invention confer permanent hydrophilicity to cured polysiloxane compositions; this permanent hydrophilicity is characterized by static water contact angles that are less than the state-of-the-art 50±10° before and after washing and/or disinfection and by advancing contact angles <about 90°.

The contact angle is a thermodynamic quantity and should have a unique value for a particular system under specified conditions. However, hysteresis is often found (see C. A. Miller and P. Neogi, *Interfacial Phenomena*, Marcel Dekker, N.Y., N.Y., 1985, pp. 67–83) in contact angle measurements depending on the direction of movement of the interface relative to its interacting surface. When an interface advances along a fresh surface, the advancing contact angle (typically designated $\theta_A$) is larger than the receding contact angle (typically designated $\theta_R$). In general, $\theta_A \geq \theta \geq \theta_R$. Advancing and receding angles may differ by as many as 60 degrees. $\theta_A$ for water in contact with silicones is greater than 120 degrees. For measurements made on fresh surfaces under dynamic conditions, hydrophilicity is indicated by $\theta_A$ less than about 100 degrees.

EXAMPLES

The following illustrative examples describe the instant invention in more detail. They are not intended to limit the scope of the specification and the claims.

Abbreviations used in the description of the illustrative examples are defined in the following table.

| ABBREVIATION | MEANING | ABBREVIATION | MEANING |
| --- | --- | --- | --- |
| M | $(CH_3)_3SiO_{1/2}$ | EO | ethylene oxide |
| D | $(CH_3)_2SiO_{2/2}$ | PO | propylene oxide |
| D' | $CH_3SiHO_{2/2}$ | BO | butylene oxide |
| M' | $(CH_3)_2SiHO_{1/2}$ | IPM | isopropyl myristate |
| $M^{VI}$ | $H_2C=CH(CH_3)_2SiO_{1/2}$ | IPP | isopropyl palmitate |
| gc/ms | gas chromatography/mass spectrometry | $\theta$ | water contact angle |
| ICP | inductively coupled plasma spectroscopy | gc | gas chromatography |
| gpc | gel permeation chromatography | MVC | mixture of cyclic methylvinylsiloxanes |

EXAMPLES

MATERIALS

Trimethylsiloxy terminated polysiloxane-polyether copolymers were prepared by hydrosilylation using the procedures of the patents cited in the Table 1. Copolymers A–E contain fewer than 10 silicon atoms per molecule. They were converted to unsaturated derivatives for imparting permanent hydrophilicity to polysiloxane compositions. Copolymers F–J were employed as compatibilizing agents.

TABLE 1

POLYSILOXANE - POLYETHER COPOLYMERS USED AS STARTING MATERIALS

| PRODUCT | SILOXANE BACKBONE | POLYETHER | SYNTHESIS METHOD |
|---|---|---|---|
| A | MD'M | $H_2C=CHCH_2(EO)_{7.5}OCH_3$ | U.S. Pat. No. 3,299,112 |
| B | MD'M | $H_2C=CHCH_2(EO)_{5.5}(PO)_{2.8}OH$ | U.S. Pat. No. 5,191,103 |
| C | $MD_4D'M$ | $H_2C=CHCH_2(EO)_{3.23}OCH_3$ | U.S. Pat. No. 4,847,398 |
| D | $D_4D'$ | $H_2C=CHCH_2(EO)_{7.5}OCH_3$ | U.S. Pat. No. 3,507,815 |
| E | $D_4D'$ | $H_2C=CHCH_2(EO)_{5.5}(PO)_{2.8}OH$ | U.S. Pat. No. 5,191,103 |
| F | MD'M | $H_2C=CHCH_2(PO)_{1.8}OH$ | U.S. Pat. No. 4,847,398 |
| G | MD'M | $H_2C=CHCH_2(PO)_{2.5}OH$ | U.S. Pat. No. 4,847,398 |
| H | MD'M | $H_2C=CHCH_2(EO)_{12}(PO)_3OH$ | U.S. Pat. No. 4,847,398 |
| I | $MD_7D'_3M$ | $H_2C=CHCH_2(PO)_{11.8}OC_4H_9$ | U.S. Pat. No. 4,847,398 |
| J | $MD_{22}D'_{3.2}M$ | $H_2C=CHCH_2(EO)_{7.5}OCH_3$ | U.S. Pat. No. 3,507,815 |

1,3-Divinyltetramethyldisiloxane (M*M*) was purchased from Gelest, Inc. A methylvinylcyclosiloxane mixture, $[H_2C=CH(CH_3)SiO]_q$, q=3(4.3 wt %/), q=4(76.54 wt %), q=5(17.68 wt %), q=6(1.4 wt %) was prepared by hydrolysis of $H_2C=CH(CH_3)SiCl_2$.

Cyclo(dimethylsiloxane-co-methylhydrogenosiloxanes) of the type $D_xD'_y$(x=1–5, y=1–4, x+y<8) were prepared by the acid-catalyzed equilibration of polydimethylsiloxanes and polymethylhydrogensiloxanes as described by Chang and Buese in *Polmer Preprints*, 33 (1992) 160–161.

IPM and IPP are commercial materials purchased from Aldrich Chemical Co., Inc.

SILWET®L-77 is a siloxane-polyether copolymer with terminal trimethylsiloxy groups.

V-2K is an α, ω-divinylpolydimethylsiloxane having 0.22 wt % vinyl and a viscosity of 2000 cSt at 25° C.

V-200 is a α, ω-divinylpolydimethylsiloxane with 0.7 wt % vinyl and a viscosity of 200 cSt at 25° C.

V-XL is a crosslinker with SiH content 40 cc $H_2$/g

VCAT-RT is a platinum complex of 1,3-divinyltetramethyldisiloxane dissolved in 500 cSt silicone oil. Its Pt content is ~2 wt %.

SILWET®L-77, V-2K, V-200, V-XL and VCAT-RT are all manufactured by the Organosilicones Group of Witco Corp. AEROSIL®200, AEROSIL®300 and AEROSIL®R-812 are silicas manufactured by Degussa. AEROSIL®200 is hydrophilic, has a surface area of 200 $m^2$/g , median particle size ~8 nm and average particle size 12 nm. AEROSIL®300 is also hydrophilic with surface area 300 $m^2$/g, median particle size ~6 nm and average particle size 7 nm. AEROSIL®R-812 is hydrophobic, has surface area 260 $m^2$/g, median particle size ~7 nm and average particle size 7 nm.

BANICIDE®, a glutaraldeyhde-based, sterilizing disinfectant manufactured by Pascal Co. Inc., was used as the disinfecting medium in accordance with the manufacturer's instructions. Disinfection time was overnight (~16 hr) in most cases and in others as long as 64 hr. Commercial dental impression formulations were mixed and cured as directed in the manufacturer's product literature.

$(CH_3)_4N^{+-}OSi(CH_3)_2[OSi(CH_3)_2]_{58}Si(CH_3)_2O^{-+}N(CH_3)_4$(N-CAT) was prepared by charging 216 g $[(CH_3)_2SiO]_4$, 18.1 g $(CH_3)_4NOH.5H_2O$ and 250 g toluene to three-necked 1 L round bottom flask fitted with a temperature-controlled heating mantle, mechanical stirrer, Claisen connection, water cooled Friedrich condenser, thermometer, and vacuum take-off line. The mixture was heated to 65–70° C. at 100–200 torr to remove the water-toluene azeotrope. When no additional azeotrope distilled over, the water and toluene were separated and the weight of water (~8 g) recorded. The vacuum was released, the temperature was lowered and another 100 g toluene added to the flask. Final stripping of residual water (~1 g) and all of the toluene was accomplished by heating to 90° C. at 50 torr. The product is a viscous, hygroscopic liquid.

GENERAL SYNTHESIS PROCEDURE

Equilibration and ring opening reactions were performed in a three-necked 500 mL round bottom flask fitted with a temperature-controlled heating mantle, mechanical stirrer, Claisen connection, water cooled Friedrich condenser, thermometer, and nitrogen sparge line. Weighed quantities of polysiloxane-polyether copolymer, vinylsiloxane and N-CAT were charged to the flask and the stirring contents heated to 90° C. for 4 hours. The temperature was increased to 140° C. for 1 hour to decompose N-CAT and the reaction mixture was later stripped in vacua at 100° C./4 torr for 4 hours. Condensate was collected, weighed and analyzed by gc and gc/ms. The stripped product was weighed and analyzed by $^{13}C$ and $^{29}Si$ nmr, gpc and ICP. It was used as a hydrophilic additive and as a silicone surfactant

EVALUATION OF HYDROPHILICITY

Hydrophilicity was evaluated by measuring the static water contact angle, as a function of time, on the surfaces of cured polysiloxane discs containing the unsaturated polysiloxane-polyether copolymers of this invention. Contact angles were also measured on control discs made without the inventive hydrophilic additives and on samples made from commercial compositions advertized as being hydrophilic. All measurements were made with a Ramé-Hart goniometer (Model 100 00 115). Standard deviations of the measured angles were ±5°.

Hydrophilicity was evaluated by measuring the water contact angle, as a function of time, on the surfaces of cured polysiloxane discs containing the unsaturated polysiloxane-polyether copolymers of this invention. Contact angles were also measured on control discs made without the inventive hydrophilic additives and on samples made from commercial compositions advertised as being hydrophilic. All measurements were made with a Ramé-Hart goniometer (Model 100 00 115). Standard deviations of the measured angles were ±5°.

Dynamic contact angle measurements were made with a Cahn DCA-315 dynamic contact angle analyzer. The two part formulation was mixed and applied to the glass plate of the analyzer. Measurements were taken while the formulation was curing. Calculation of the advancing and receding contact angles were made automatically by the analyzer software.

Examples 1–5

Examples 1–5 illustrate the synthesis of vinyl-containing polysiloxane-polyether copolymers by the general procedure described above. Reaction stoichiometry was varied as shown in Table 2 using the quantities of saturated polysiloxane-polyether copolymers of Table 1 and 1,3-divinyltetramethyldisiloxane (M*M*). All reactions were run at 85–90° C./4 hr prior to catalyst decomposition and separation of volatiles.

TABLE 2

SYNTHESIS OF VINYL-CONTAINING POLYSILOXANE-POLYETHER COPOLYMERS

| EXAMPLE | PRODUCT, g (see Table 1) | $M^{VI}M^{VI}$, g | N-CAT, g | STRIPPED PRODUCT, g |
|---|---|---|---|---|
| 1 | A,120.9 | 36 | 0.5 | 112 |
| 2 | B,132.6 | 36 | 0.5 | 124 |
| 3 | C,67.7 | 17.5 | 0.1 | 64.2 |
| 4 | D,98.4 | 24 | 0.4 | 96.5 |
| 5 | E,98.6 | 21 | 0.4 | 100.2 |

Examples 7–34

Examples 7–34 illustrate the use of the three categories of compatibilizers to prepare homogeneous blends of the hydrophilic, unsaturated polysiloxane-polyether copolymers of Examples 1 and 2 with α,ω-divinylpolydimethylsiloxanes (V-2K). IPM and IPP are representative of the hydrocarbon ester compatibilizers. AEROSIL®200 (A-200) and AEROSIL®300 (A-300) are representative of the hydrophilic silica compatibilizers and AEROSIL®R-812 is representative of the hydrophobic silica compatibilizers. The copolymers F, H, I and J of Table 1 exemplify the polysiloxane-polyether copolymer compatibilizers.

Samples were prepared by vigorously mixing weighed quantities of V-2K and compatibilizer at 1500 rpm for 30 min. The hydrophilic, unsaturated copolymer from Examples 1 or 2 was added slowly (dropwise) under moderate stirring at 800 rpm. Mixing was continued for another 30 min after the addition was completed. Samples were left undisturbed at room temperature and inspected for phase separation periodically. The experimental results are summarized in Table 4.

Mixtures of V-2K and the hydrophilic, unsaturated trisiloxane copolymers prepared in Examples 1 and 2 were immiscible. Table 4 shows that the various compatibilizers used effected stable miscibility of these mixtures to different extents. Examples 10–12 and 20–21 show that 10 wt % IPP was required to keep 2–4 wt % of the hydrophilic unsaturated 15 trisiloxanes fully homogenized for two or more months. Phase separation was evident at shorter times with lower concentrations (Example 10) of the ester. Miscibility was also realized with IPM (Examples 7–9 and 19), but it was less durable even with the use of 15 wt % of the ester and 2 wt % of the hydrophilic, unsaturated trisiloxane.

Results of Examples 13–15 and 22–28 reveal that the high surface area hydrophilic silicas, AEROSIL®200 and AEROSIL®300, were very effective at compatibilizing mixtures of V-2K and the hydrophilic, unsaturated trisiloxane copolymers. 1–2 wt % of these solids afforded more than three months stability in mixtures containing up to 10 wt % trisiloxane. Mixtures (see Examples 16 and 29) containing 4 wt % hydrophilic, unsaturated trisiloxane in V-2K were stabilized for up to three weeks with 2 wt % of the hydrophobic silica, Aerosil®R-812.

Copolymers F, H, I and J were also not equally effective in providing storage stability of the mixtures of V-2K and the hydrophilic, unsaturated trisiloxane copolymers. Copolymer F in which the polyether was an uncapped propylene oxide sequence gave mixtures (Examples 17 and 30–32) that were stable for more than three months. 10 wt % of Copolymer F solubilized 4 wt % of the trisiloxanes in V-2K.

TABLE 4

COMPATIBILIZATION OF HYDROPHILIC UNSATURATED COPOLYMERS AND α, ω-DIVINYLPOLYDIMETHYLSILOXANE (V-2K)

| EXAMPLE | HYDROPHILIC ADDITIVE | COMPATIBILIZER, | V-2K, g | RESULTS |
|---|---|---|---|---|
| 7 | Ex.1, 2 g | IPM, 6 g | 92 | stable 1 day |
| 8 | Ex.1, 2 g | IPM, 10 g | 88 | stable 4 days |
| 9 | Ex.1, 2 g | IPM, 15 g | 83 | stable 4 days |
| 10 | Ex.1, 2 g | IPP, 6 g | 92 | stable 3 weeks |
| 11 | Ex.1, 2 g | IPP, 10 g | 88 | stable > 2 months |
| 12 | Ex.1, 4 g | IPP, 10 g | 86 | stable 1 month |
| 13 | Ex.1, 4 g | A-200, 2 g | 94 | stable > 10 months |
| 14 | Ex.1, 10 g | A-200, 2 g | 88 | stable > 10 months |
| 15 | Ex.1, 10 g | A-300, 2g | 88 | stable > 10 months |
| 16 | Ex.1, 4 g | R-812, 2 g | 94 | stable 3 weeks |
| 17 | Ex.1, 4 g | Copolymer F, 10 g | 86 | stable > 3 months |
| 18 | Ex.1, 2 g | Copolymer, I, 10 g | 88 | stable 1 week |
| 19 | Ex.2, 2 g | IPM, 15 g | 83 | stable 1 week |
| 20 | Ex.2, 2 g | IPP, 10 g | 88 | stable > 2 months |
| 21 | Ex.2, 4 g | IPP, 10 g | 86 | stable > 2 months |
| 22 | Ex.2, 2 g | A-200, 1 g | 97 | stable > 3 months |
| 23 | Ex.2, 4 g | A-200, 1 g | 95 | stable > 2 months |
| 24 | Ex.2, 4 g | A-200, 2 g | 94 | stable > 10 months |
| 25 | Ex.2, 6 g | A-200, 2 g | 92 | stable > 10 months |
| 26 | Ex.2, 8 g | A-200, 2 g | 90 | stable > 10 months |
| 27 | Ex.2, 10 g | A-200, 2 g | 88 | stable > 10 months |
| 28 | Ex.2, 10 g | A-300, 2 g | 88 | stable > 3 months |
| 29 | Ex.2, 4 g | R-812, 2 g | 94 | stable 3 weeks |
| 30 | Ex.2, 2 g | Copolymer F, 2 g | 96 | stable 2 weeks |
| 31 | Ex.2, 2 g | Copolymer F, 6 g | 92 | stable 4 weeks |

TABLE 4-continued

COMPATIBILIZATION OF HYDROPHILIC
UNSATURATED COPOLYMERS AND α, ω-
DIVINYLPOLYDIMETHYLSILOXANE (V-2K)

| EXAMPLE | HYDROPHILIC ADDITIVE | COMPATIBILIZER, | V-2K, g | RESULTS |
|---|---|---|---|---|
| 32 | Ex.2, 4 g | Copolymer F, 10 g | 86 | stable > 10 months |
| 33 | Ex.2, 2 g | Copolymer J, 10 g | 88 | stable 1 week |
| 34 | Ex.2, 2 g | Copolymer H, 10 g | 88 | stable 2 weeks |

Examples 35–39

Examples 35–39 illustrate the preparation of two-part formulations, wherein PART B comprises a homogeneous blend containing a hydrophilic, unsaturated polysiloxane-polyether copolymer and a compatilizing agent such as a hydrocarbon ester, a hydrophobic or hydrophilic silica of surface area greater than 100 square meters per gram and of median particle size less than 20 nanometers, or a polysiloxane-polyether copolymer wherein the polyether contains greater than 80 weight percent hydrophobic oxyalkylene units.

The five separate PART B compositions are described in Table 5. The mixtures were prepared by the same method used in Examples 7–34 above. They were all still fully homogeneous when cured separately (see Examples 40–44) with PART A after storage at room temperature for the periods shown in Table 5. Cured samples were also prepared weekly during the course of the experiment. Static water contact angles on all five cured elastomers were <20° and remained so within experimental error (±3°) before and after disinfection in all cases.

TABLE 5

PART B COMPOSITIONS CONTAINING
COMPATIBILIZERS AND THE HYDROPHILIC UNSATURATED
TRISILOXANE OF EX. 2

| INGREDIENT | Ex. 35 | Ex. 36 | Ex. 37 | Ex. 38 | Ex 39 |
|---|---|---|---|---|---|
| V-2K, wt % | 64.07 | 82.38 | 82.38 | 82.38 | 64.07 |
| V-200, wt % | 5.73 | 7.36 | 7.36 | 7.36 | 5.73 |
| VCAT-RT, wt % | 0.08 | 0.11 | 0.11 | 0.11 | 0.08 |
| MVC, wt % | 0.12 | 0.15 | 0.15 | 0.15 | 0.12 |
| IPP, wt % | 25.00 | | | | |
| Aerosil ® R-812, wt % | | 5.00 | | | |
| Aerosil ® 200, wt % | | | 5.00 | | |
| Aerosil ® 300, wt % | | | | 5.00 | |
| Copolymer F, wt % | | | | | 25.00 |
| Trisiloxane, Ex.2, wt % | 5.00 | 5.00 | 5.00 | 5.00 | 5.00 |
| STABILITY | >2 months | 3 weeks | >10 months | >3 months | >10 months |

Examples 40–44

These examples illustrate the permanent hydrophilicity of the cured polysiloxane compositions prepared from the storage stable PART B compositions described in Examples 35–39.

PART A of the formulation contained 86.8 wt % V-2K and 13.2 wt % V-XL. Curing was done by mixing PART A and each PART B in a 1.5:1 weight ratio, pouring the mixture into a cylindrical mold and heating the mold at 120° C. for 15–30 min. Water contact angle measurements were made versus time on the cooled, elastomeric disc before and after disinfection. The 3 minute values are set forth in Table 6.

TABLE 6

DURABLE HYDROPHILICITY OF CURED
POLYSILOXANES MADE WITH HYDROPHILIC PART B
COMPOSITIONS

| EXAMPLE | PART B | θ, BEFORE DISINFECTION | θ AFTER DISINFECTION |
|---|---|---|---|
| 40 | Example 35 | 16° | 18° |
| 41 | Example 36 | 18° | 19° |
| 42 | Example 37 | 16° | 18° |
| 43 | Example 38 | 16° | 18° |
| 44 | Example 39 | 15° | 17° |

The data of Table 6 show that the contact angles were essentially unchanged before and after disinfection. The low values of the contact angles indicate that the surfaces of the cured polysiloxane compositions were made very hydrophilic by the unsaturated trisiloxane copolymers prepared in Example 2. All samples showed <0.05 wt % weight change after disinfection indicating that surface wettability was not accompanied by subsequent water absorption. The results also show that PART B compositions comprising the compatibilizing agents and hydrophilic additives of the instant invention and divinylpolysiloxanes are storage and performance stable.

Examples 45–47

These Examples illustrate the hydrophilicity of polysiloxane compositions prepared with the unsaturated copolymer composition of Example 4. Both dynamic and static hydrophilicity are exemplified.

Table 7 sets forth the two part unfilled polysiloxane formulation used to prepare the compositions tested in these examples. The two parts were mixed in the weight ratio, 1.5 parts A to 1.0 part B, along with the quantities of the hydrophilic additive of Example 4 and the mixture applied to glass plates used for the measurement of dynamic wettability with the Cahn DCA-315 contact angle analyzer. Some of the remaining mixture was poured into a cylindrical mold and cured at 120° C. for 15–30 min. The Ramé-Hart goniometer was used to measure the two minute static water contact angles on a flat surface of the cured disc. Table 8 summarizes the experimental data. The percentages of hydrophilic additive are based on the total weight of the composition.

TABLE 7

COMPOSITION OF UNFILLED, TWO PART FORMULATION

| INGREDIENT | PART A, wt % | PART B, wt % |
|---|---|---|
| V-2K | 86.8 | 91.53 |
| V-200 | — | 8.18 |
| V-XL | 13.2 | — |
| VCAT-RT | — | 0.12 |
| MVC | — | 0.17 |

In the absence of the hydrophilic additive (Example 45 of Table 8), the polysiloxane composition displayed classic hydrophobic surface behavior. The advancing dynamic contact angle, $\theta_A$, and the two minute static contact angle were both >100°. The compositions of Examples 46 and 47 contained ≧2 wt % of the hydrophilic additive of Example 5. They exhibited surface hydrophilicity and fast wettability. Advancing contact angles were <100° and two minute static values were <40°.

TABLE 8

HYDROPHILICITY OF POLYSILOXANE COMPOSITIONS CONTAINING THE ADDITIVE OF EXAMPLE 4

| EXAMPLE | ADDITIVE, wt % | $\theta_A$, degrees | $\theta_R$, degrees | Static Contact Angle, degrees |
|---|---|---|---|---|
| 45 | 0 | 113 | 84 | 105 |
| 46 | 2 | 98 | 73 | 36 |
| 47 | 4 | 84 | 73 | 10 |

We claim:

1. A composition comprising a first component comprising:
   (a) a polydiorganosiloxane that contains at least two hydrosilylatable unsaturated hydrocarbon groups per molecule;
   (b) an effective amount of hydrosilylation catalyst;
   (c) a hydrophilic, unsaturated polysiloxane-polyether copolymer having from 2 to 5 silicon atoms, at least one aliphatic unsaturation and at least one-polyether functionality; and
   (d) a compatibilizing additive.

2. A composition according to claim 1 wherein component (c) is selected from the group consisting of:
   (A) $R^1$—$SiR_2O(SiR_2$—$O)_p$—$(SiR^2Z$—$O)_m$—$SiR_2R^1$
   (B) $R^1$—$SiR_2O(SiR_2$—$O)_p$—$(SiR^2Z$—$O)_m$—$SiR_3$
   (C) $R_3SiO(SiR_2$—$O)_p$—$(SiR^2Z$—$O)_{m-(SiR^2R^1}$—$O)_q$—$SiR_3$
   (D) $R^1$—$R_2SiO(SiR_2$—$O)_p$—$(SiR^2Z$—$O)_m$—$(SiR^2R^1$—$O)_q$—$SiR_3$
   (E) $R^1$—$R_2SiO(SiR_2$—$O)_p$—$(SiR^2Z$—$O)_m$—$(SiR^2R^1$—$O)_q$—$SiR_2R^1$
   (F) $Z$—$SiR_2O(SiR_2$—$O)_p$—$(SiR^2R^1$—$O)_q$—$SiR_2R^1$
   (G) $[Z$—$SiR_2O(SiR_2$—$O)_p]_r$—$(SiR_2$—$O)$—$(SiR^2R^1$—$O)_q$—$SiR_2R^1$
   (H) $(R_2Si$—$O)_p$—$(SiR^2Z$—$O)_m$—$(SiR^2R^1$—$O)_q$
   (I) $R^1Si[(O$—$SiR_2)_p$—$Z]_3$
   (J) $RSi[(O$—$SiR^2R^1)_q$—$(O$—$SiR_2)_p$—$Z]_3$; and
   (K) $[R^1SiR_2O(SiR_2$—$O)_p]_v$—$(SiO_2)[(O$—$SiR^2R^1)_q(O$—$SiR_2Z)_m]_{4-v}$
   wherein R is a $C_1$-$C_{20}$, saturated, monovalent organic group; $R^1$ is a $C_1$-$C_{20}$, unsaturated monovalent organic group that can be hydrosilylated to yield silicon-carbon bonds; $R^2$ may be the same as R or as $R^1$; m, p, q, r and v are chosen such that the total number of silicon atoms per molecule is 2 to 5 inclusive with the proviso that there is at least one Z and at least one $R^1$ per molecule and r and v are values from 0 to 1, 3≧m>0, and 0≦q and p≦3; and Z is a polyether-containing group that is linked to the polysiloxane block by a silicon-carbon bond.

3. A composition according to claim 2 wherein Z has general formula of the type,
   —$C_xH_{2x}O(C_aH_{2a}O)_bR''$ and —$C_xH_{2x}OG[(C_aH_{2a}O)_bR'']_z$
   wherein x is an integer in the range 1–20, a is an integer having a value greater than or equal to 2, G is a polyhydroxy group capable of being alkoxylated; z is the valency of G, R'' is hydrogen or a polyether capping group, an alkyl group of 1–8 carbon atoms, or an acyl group of 1–8 carbon atoms, or a vinyl ether or an organosilyl group.

4. A composition according to claim 3 wherein component (c) is selected from the group consisting of:
   $H_2C$=$CHSi(CH_3)_2$—$O$—$Si(CH_3)Z$—$O$—$Si(CH_3)_2CH$=$CH_2$;
   $H_2C$=$CHSi(CH_3)_2$—$O$—$Si(CH_3)Z$—$O$—$Si(CH_3)_3$;
   $H_2C$=$CHSi(CH_3)_2$—$O$—$Si(CH_3)Z$—$O$—$Si(CH_3)_2CH$=$CH_2$;
   $H_2C$=$CHSi(CH_3)_2$—$O$—$[Si(CH_3)_2O]_2$—$[Si(CH_3)Z$—$O]$—$Si(CH_3)_2CH$=$CH_2$; and
   $H_2C$=$CHSi(CH_3)_2$—$O$—$[Si(CH_3)_2O]$—$[Si(CH_3)Z$—$O]_2$—$Si(CH_3)_2CH$=$CH_2$; wherein
   Z=—$(CH_2)_3O(C_2H_4O)_{7.5}CH_3$ or $(CH_2)_3O(C_2H_4O)_5(C_3H_6O)_2H$ or —$(CH_2)_3O(C_2H_4O)_3CH_3$ or $HO(C_2H_4O)(CH_2C$=$CHCH_2)(OC_2H_4)OH$.

5. A composition according to claim 1 wherein the first component additionally comprises a rheology modifier.

6. A composition according to claim 1 wherein the compatabilizing additive is selected from the group consisting of: a hydrocarbon ester with solubility parameter, $\delta,$=13–17 MPa½, or a polysiloxane-polyether copolymer, or a hydrophobic or hydrophilic filler with surface area greater than 100 square meters per gram and median particle size smaller than 20 nanometers.

7. A composition according to claim 1 additionally comprising a separate, second part which comprises:
   (a) a polyorganohydridosiloxane crosslinker that contains at least three SiH bonds per molecule, and
   (b) a polydiorganosiloxane that contains at least two hydrosilylatable unsaturated hydrocarbon groups per molecule.

8. The reaction product according to claim 7 wherein the first and second components are combined and allowed to react.

9. A composition according to claim 7 wherein the second component additionally comprises a polyorganohydridosiloxane chain extender with terminal SiH groups.

10. The process of combining the first and second components of claim 7.

* * * * *